United States Patent [19]

Lee et al.

[11] Patent Number: 5,639,439

[45] Date of Patent: Jun. 17, 1997

[54] GALLIUM DIMERCAPTOSUCCINATE AS A NOVEL TUMOR IMAGING AGENT

[75] Inventors: Te-Wei Lee; Wei-Lian Chen; Ming-Der Yu, all of Taipei; Lie-Hang Shen, Tau Yen; Zei-Tsan Tsai, Tau Yen; Shyh-Yi Chyi, Tau Yen, all of Taiwan

[73] Assignee: Institute of Nuclear Energy Research, Taiwan, Taipei, Taiwan

[21] Appl. No.: 356,895

[22] Filed: Dec. 15, 1994

[51] Int. Cl.$^6$ ............................. A61K 51/00; A61M 36/14
[52] U.S. Cl. ................. 424/1.11; 424/1.37; 424/1.65; 424/9.6; 534/10
[58] Field of Search ....................... 424/1.69, 9.6, 424/1.11, 1.37, 1.53, 1.65, 9.1; 534/10

[56] References Cited

U.S. PATENT DOCUMENTS

| | | | |
|---|---|---|---|
| Re. 31,463 | 12/1983 | Loberg et al. | 424/1.69 |
| 4,017,596 | 4/1977 | Loberg et al. | 424/1.69 |
| 4,233,285 | 11/1980 | Winchell et al. | 424/1.69 |
| 4,264,468 | 4/1981 | Neirinckx et al. | 424/1.69 |
| 4,361,544 | 11/1982 | Goldenberg | 424/1.21 |
| 4,448,763 | 5/1984 | Triplett | 424/1.61 |
| 4,720,379 | 1/1988 | Heyl et al. | 424/10 |
| 5,019,369 | 5/1991 | Presant et al. | 424/1.49 |
| 5,079,346 | 1/1992 | Kung | 534/10 |
| 5,399,338 | 3/1995 | Born et al. | 424/1.49 |
| 5,428,139 | 6/1995 | Kiefer et al. | 534/10 |

OTHER PUBLICATIONS

Saji et al (1980). Radioisotopes, vol. 29, No. 1, pp. 7–12 "Enhancement of $^{67}$Ga–Citrate Tumor-to-Blood Ratios by Chelating Agent".

Green et al. "Gallium–68 1,1,1–tris (5–methoxysalicylaldiminomethyl) Ethane: A Potential Tracer for Evaluation of Regional Myocardial Blood Flow", The Journal of Nuclear Medicine, 26, pp. 170–180 (1995).

Burns et al. "Reversal of Gallium Arsenide–Induced Suppression of the Antibody Response by a Mixed Disulfide Metabolite of Meso –2,3–dimelcaptosuccinic acid." The Journal of Pharmacology and Experimental Therapeutics, vol. 264, No. 2, pp. 695–700.

Green et al, "Gallium Radiopharmaceutical Chemistry," Nucl. Med. Bio. vol. 6, No. 5, pp. 435–448 (1989).

Chemical Principles, ©1985, p. 237. "The Periodic Table and the Properties of Metals" by Masterton et al. The Merck Index, 9th edition, p. 560, compound 4191.

Primary Examiner—John Kight
Assistant Examiner—Dameron L. Jones
Attorney, Agent, or Firm—Burns, Doane, Swecker & Mathis, LLP

[57] ABSTRACT

Novel tumor imaging agents in which the dimercaptosuccinic acid was dissolved in phosphate buffer and labelled with radioisotope gallium. The product of gallium dimercaptosuccinate has been characterized by a variety of experiments including serum stability, biodistribution and imaging experiment. As the results, the compound of gallium dimercaptosuccinate has been confirmed as a novel radiopharmaceutical for tumor imaging agent.

4 Claims, 2 Drawing Sheets

GALLIUM DIMERCAPTOSUCCINATE AS A NOVEL TUMOR IMAGING AGENT

FIELD OF INVENTION

The present invention relates to a radionuclide gallium complex of dimercaptosuccinic acid as radiopharmaceuticals for tumor imaging agent.

BACKGROUND OF THE INVENTION

Radioisotope gallium-labelled radiopharmaceuticals have been applied in nuclear medical diagnosis, e.g., $^{67}$Ga-citrate for tumor and abscess imaging, $^{68}$Ga-EDTA for detection of blood-brain barrier defect, $^{68}$Ga-tripolyphosphate for bone scanning, $^{67}$Ga-dimethylgallium (III) acetylacetonate for heart imaging. There are two gallium radioisotopes which are labelled radiopharmaceuticals. One is gallium-67 which is cyclotron produced by $^{68}$Zn(P,2n)$^{67}$Ga. The physical half-life of $^{67}$Ga is 3.3 days. Ga-67 radiopharmaceuticals have played a major role in diagnostic imaging using Single Photon Emission Computed Tomography (SPECT). The other is gallium-68 which is $^{68}$Ge/$^{68}$Ga generator-produced positron-emitting radionuclides. The physical half-life of the parent, $^{68}$Ge, is 275 days. The physical half-life of the daughter, $^{68}$Ga, is 68 min, which is labelled radiopharmaceuticals for positron emission tomography (PET). Today, the clinical application of gallium radiopharmaceuticals is the use of gallium-67 citrate for tumor and abscess imaging. The gallium-68 will dominate a role in the future, as PET imaging centers become more available.

SUMMARY OF THE INVENTION

The main object of the present invention is to provide a novel tumor imaging agent in which the dimercaptosuccinic acid was dissolved in phosphate buffer and labelled with radioisotope gallium. The product of gallium dimercaptosuccinate has been characterized by a variety of experiments including serum stability, biodistribution and imaging experiment. As the results show the compound of gallium dimercaptosuccinate has been confirmed as a novel radiopharmaceutical for tumor imaging agent.

The preparation of this novel tumor imaging agent has also proved to be more simple, more efficient and convenient than any known tumor imaging agent in the literature. The radio-gallium dimercaptosuccinate radiopharmaceutical is very good as tumor localization.

DETAILED DESCRIPTION OF THE INVENTION

Figure 1:
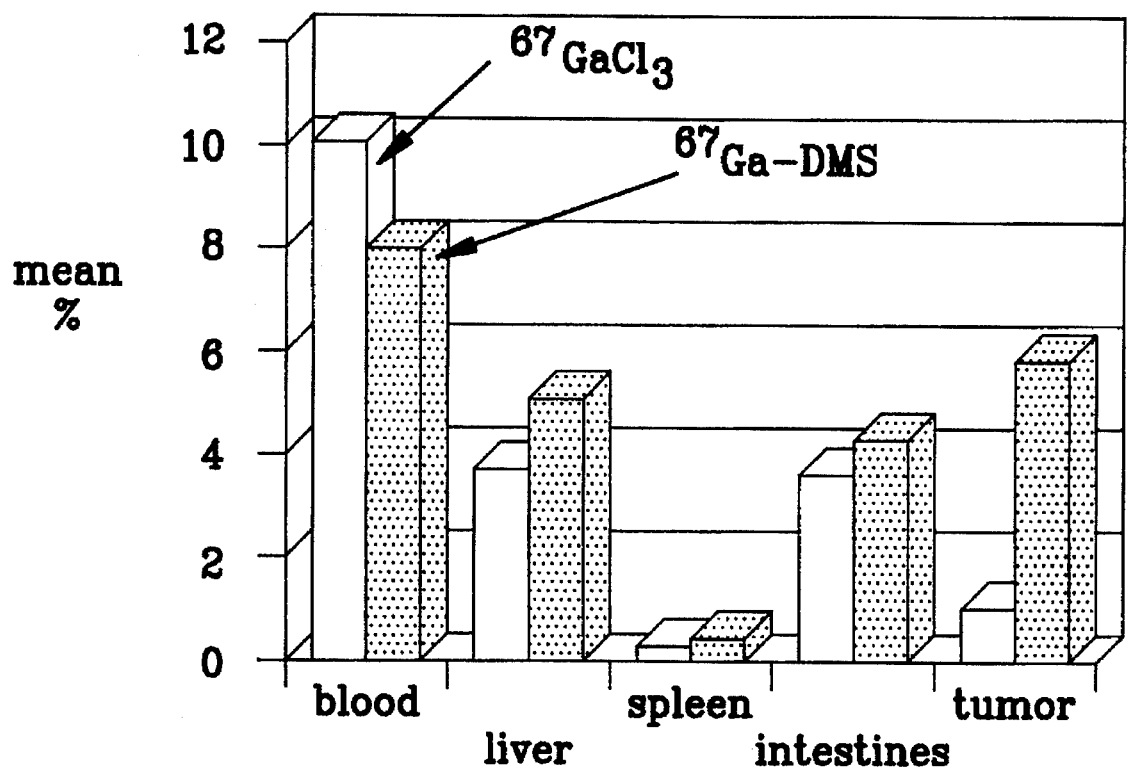
FIG. 1 is a radio activity graph measured on various organs of the body of an athymic nude mouse after implantation of viable cultured cells and glioblastoma and after the injection of gallium-67 dimercaptosuccinate.

The present invention can be further described by the following examples.

EXAMPLE 1

Preparation of Gallium-67 Chloride

The original source of $^{67}$Ga was $^{67}$Ga citrate (6 mCi, E.I. du Pont). To 3 ml of gallium-67 citrate was added 3 ml of distilled water, whereafter the solution was filtered over a SEP-PAK SI cartridge. The cartridge was washed three times with 5 ml distilled water to remove citrate ions. The retained radioactivity was elutriated from the cartridge with 2 ml of 0.1M HCL to yield a $^{67}$Ga chloride solution ready to be used for labelling. The recovery of $^{67}$Ga chloride was 95%.

EXAMPLE 2

Gallium-67 Chloride Labelled Dimercaptosuccinic Acid

To radiolabel dimercaptosuccinic acid with gallium-67 chloride, 1.0 mg of dimercaptosuccinic acid was dissolved in 1 ml of phosphate buffer (0.2M, ph=7.5). A solution of gallium-67 chloride (0.5 ml) was added to dimercaptosuccinate-phosphate buffer solution. The mixture solution was incubated for 5 to 10 min. Quality control was performed by paper chromatography (Whatman paper No. 1) using 40% $CH_3CN$ as a solvent. The chromatographic paper was analyzed by a radiochromatogram scanner. In this system, the gallium-67 chloride had an Rf value of 0.87 to 0.89, whereas the labelled gallium dimercaptosuccinate had an Rf value of 0. The radiolabelling yield was 100% and this preparation was directly used for the animal experiments.

EXAMPLE 3

In Vitro Serum Incubation

A sample of human serum (1 ml) was incubated at 37° C. with gallium-67 dimercaptosuccinate (0.1 ml) for 30 min. At the end of incubation the radioactivity was spotted on Whatman paper No. 1 and developed in 40% $CH_3CN$. The distribution of radioactivity was studied by scanning on a radiochromatogram. The result of radiolabelling yield was 95%. The mean was only 5% free gallium-67 chloride in the serum.

EXAMPLE 4

Animal Biodistribution Studies

The six-week old athymic nude mice were obtained from the Experiment Animal Center, Tri-service General Hospital, Taipei, Taiwan. The viable cultured cells, glioblastoma (GBM), were implanted in the upper back leg by intradermal injection. The tissue biodistribution of gallium-67 dimercaptosuccinate was determined following injection (0.15 to 0.2 ml) into tail vein of ketamine anesthetized in tumor-bearing mice. The reanesthetized animals were sacrificed immediately thereafter by decapitation at given time intervals. The organs of interest were subsequently excised, blotted with tissue paper, weighed and the radioactivity was measured. The tissue distribution of gallium-67 dimercaptosuccinate and gallium-67 chloride in tumor-bearing mice are shown in FIG. 1 at 2 hr. postinjection, as much as 7.8% and 1.1% were in GBM and gallium-67 chloride respectively.

EXAMPLE 5

Imaging Studies

Figure 2:
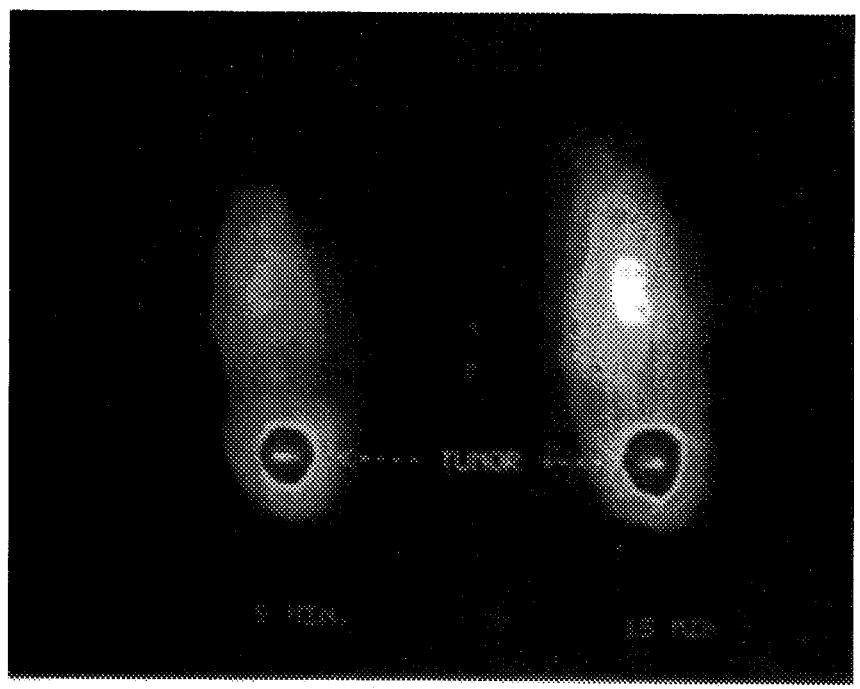
FIG. 2 is a photograph showing the position of tumors in the body of athymic nude mice imaged and 15 minutes after injection with gallium-67 dimercaptosuccinate.

Imaging was performed using the Elscint gamma camera with medium energy collimator, and a SIMIS-IV nuclear medicine computer for data processing. The gamma images of gallium-67 dimercaptosuccinate in mice at 5 min and 15 min are shown in FIG. 2. These images further confirm the tumor uptake and also the fact that the radiopharmaceutical is stable in vivo.

The file of this patent contains at least one drawing executed in color. Copies of this patent with a color drawing will be provided by the Patent and Trademark Office upon request and payment of the necessary fee.

We claim:

1. A radiopharmaceutical tumor localizing imaging agent, comprising a radiogallium labelled dimercaptosuccinic acid which is obtained by reacting dimercaptosuccinic acid with a radiogallium chloride compound in a phosphate buffer solution at a pH of about 7.5.

2. A method of using the compound of claim 1, for tumor imaging, comprising administering a tumor imaging amount of said compound to a tumor comprising subject.

3. The agent of claim 1, wherein the gallium is gallium-67.

4. The method of claim 2, wherein the gallium is gallium-67.

* * * * *